United States Patent [19]
Holder et al.

[11] Patent Number: 5,843,453
[45] Date of Patent: Dec. 1, 1998

[54] GROWTH HORMONE POTENTIATING MOLECULES

[75] Inventors: Andrew Thomas Holder, Cambridge, England; James Beattie, Ayrshire, Scotland

[73] Assignee: Biotechnology and Biological Sciences Research Council, Swindon, Great Britain

[21] Appl. No.: 392,973

[22] PCT Filed: Sep. 7, 1993

[86] PCT No.: PCT/GB93/01887

§ 371 Date: Apr. 25, 1995

§ 102(e) Date: Apr. 25, 1995

[87] PCT Pub. No.: WO94/05697

PCT Pub. Date: Mar. 17, 1994

[30] Foreign Application Priority Data

Sep. 7, 1992 [GB] United Kingdom ............... 9218907
Aug. 9, 1993 [GB] United Kingdom ............... 9316508

[51] Int. Cl.⁶ .................. A61K 39/00; C07K 14/61; C07K 7/07
[52] U.S. Cl. .................. 424/195.11; 424/193.1; 424/185.1; 424/184.1; 530/329; 530/311; 530/317
[58] Field of Search .............. 424/130.1, 139.1, 424/158.1, 184.1, 185.1, 195.11, 193.1; 530/329, 311, 317

[56] References Cited

FOREIGN PATENT DOCUMENTS 0303488  2/1989  European Pat. Off. .
59357    4/1994  European Pat. Off. .

OTHER PUBLICATIONS

Liberti, J.P.; Biochim. Biophys. Acta, vol. 675, 1981; pp. 239–247.

Chillemi, F., et al; Chemical Abstracts, vol. 89, 1978, p. 70; Abstract No. 71230.

Sato, K., et al; Chemical Abstracts, vol. 111, 1989, p. 80; Abstract No. 33758.

Aston, R., et al; Mol. Immunol., vol. 24, No. 2, 1987, pp. 143–150.

Borems et al, Biochemistry, vol. 26, pp. 7774–7778, (1987).

Poskus et al, Eur. J. Immunol., vol. 6, pp. 409–417 (1976).

Yamasaki et al, The Journal of Biol. Chem., vol. 247 (12), pp. 3874–3880, Jun. 25, 1972).

Goodfriend et al, J. Clin. Endocrinol. Outab., 30, pp. 565–572, (1970).

Shieh et al, Journal of Endocrinology, 145, pp. 169–174, (1995).

*Primary Examiner*—Ponnathapura Achutamurthy
*Assistant Examiner*—T. D. Wessendorf
*Attorney, Agent, or Firm*—Hale and Dorr LLP

[57] ABSTRACT

Antigenic molecules cause antibodies to be raised against at least some of the 91 to 102 region of a natural growth hormone when parenterally administered in vivo. The molecules can include portions of the 91 to 102 region, particularly the 94 to 98 region. The antibodies are believed to bind to growth hormone on administration and enhance its effect.

6 Claims, 13 Drawing Sheets bGH residues 91-102

|  |  |  | Relative Reactivity |
|---|---|---|---|
| Q F L ⌈S R V F T⌉ | | | + + |
| F L ⎢S R V F T⎥ N | | | + + |
| L ⎢S R V F T⎥ N S | | | + + + |
| ⎣S R V F T⎦ N S L | | | + + + + |
| R V F T N S L V | | | + |

*Fig. 2B*

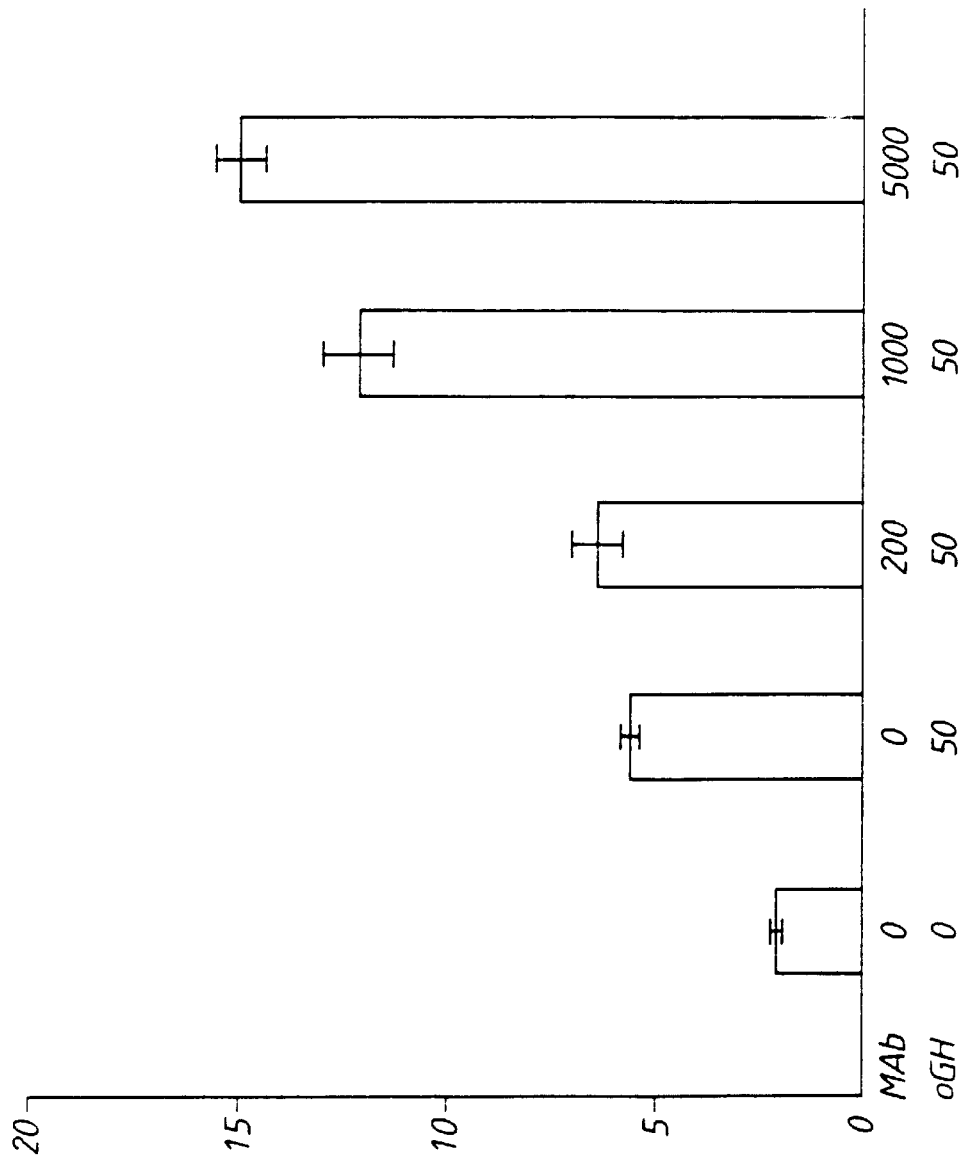

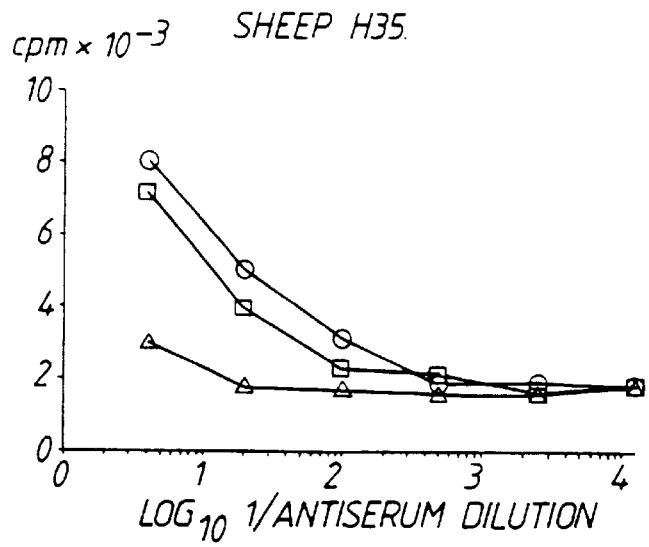
Fig. 6.1
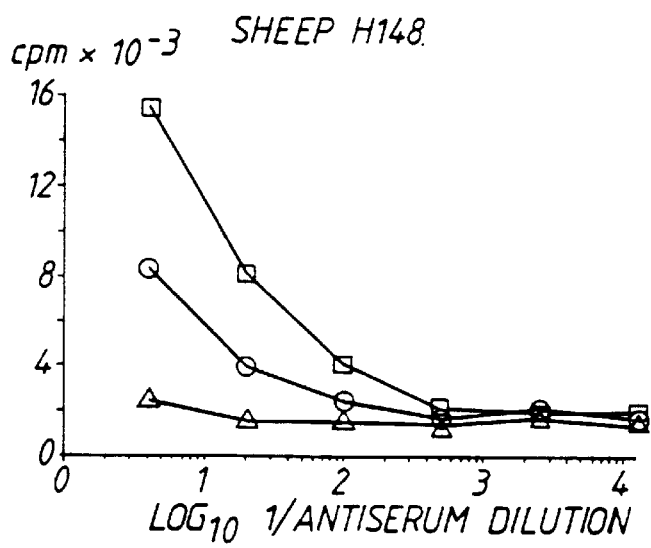
Fig. 6.2
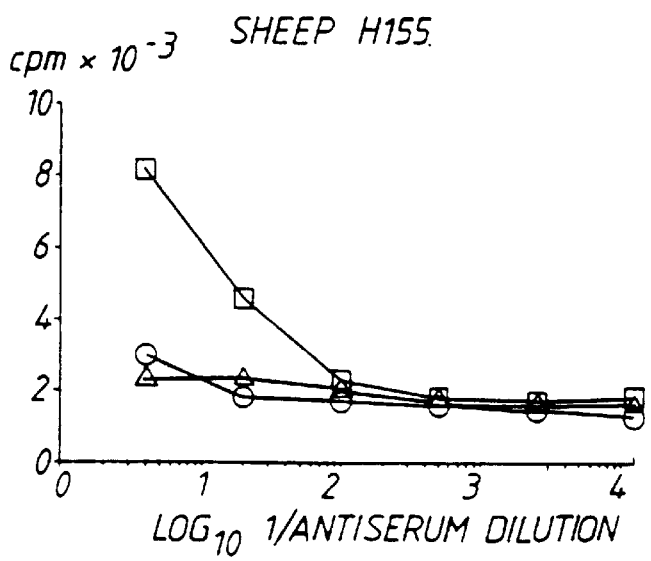
Fig. 6.3

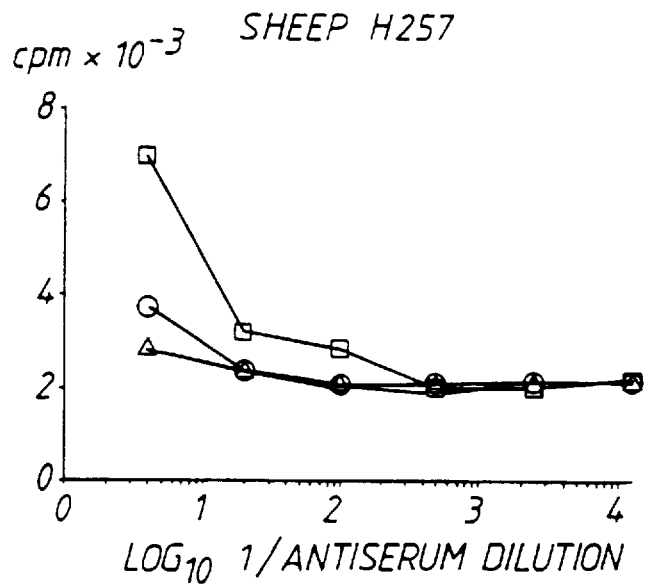
Fig. 6.4
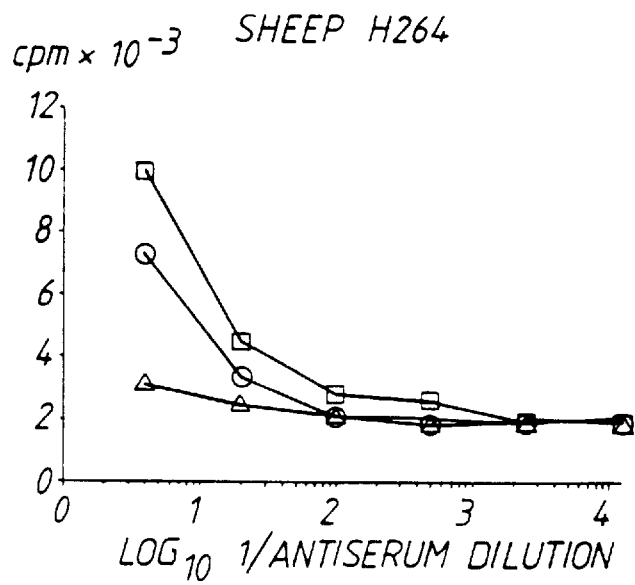
Fig. 6.5

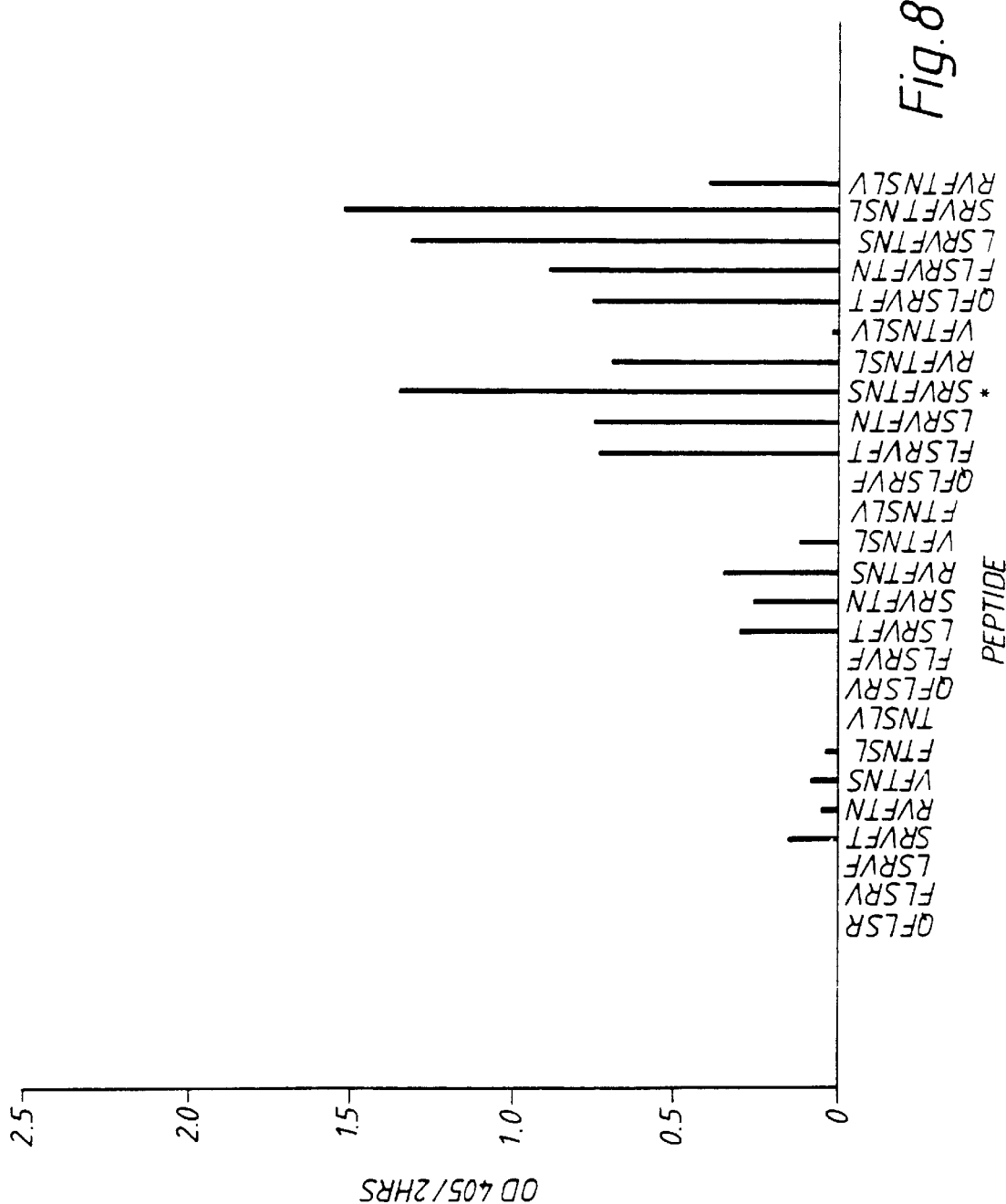

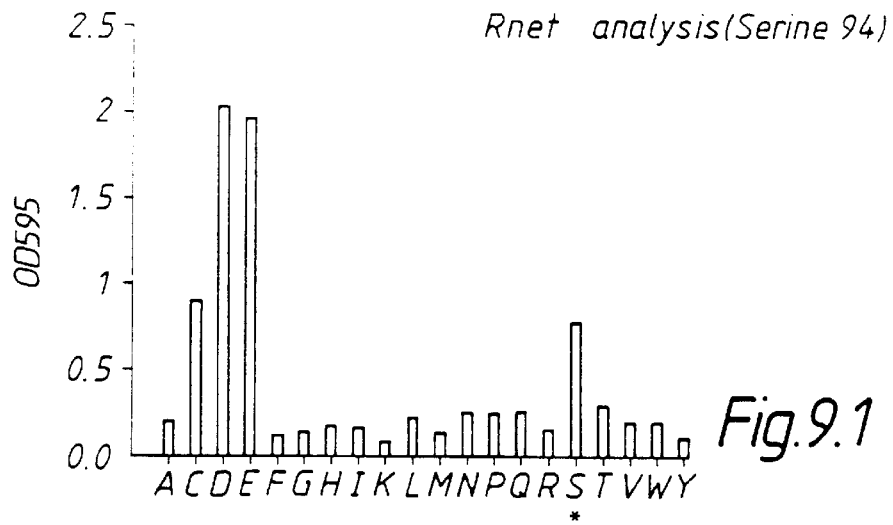
Fig. 9.1
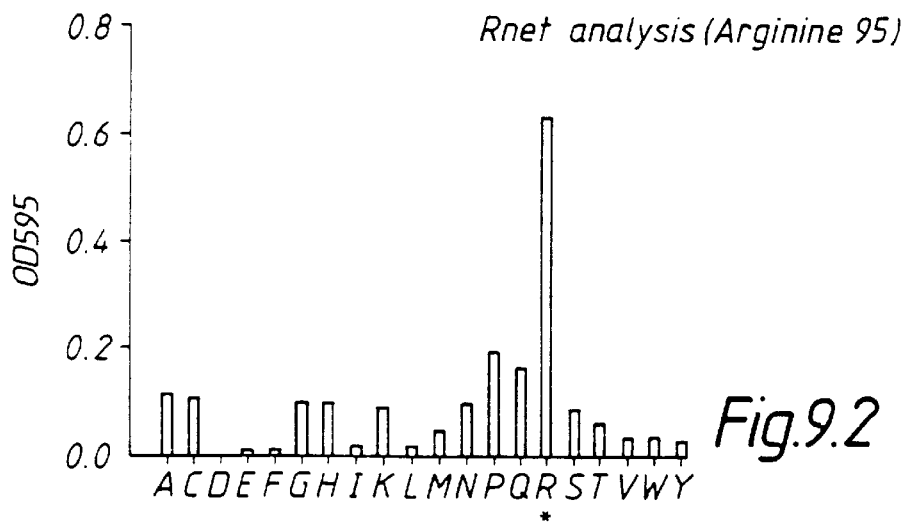
Fig. 9.2
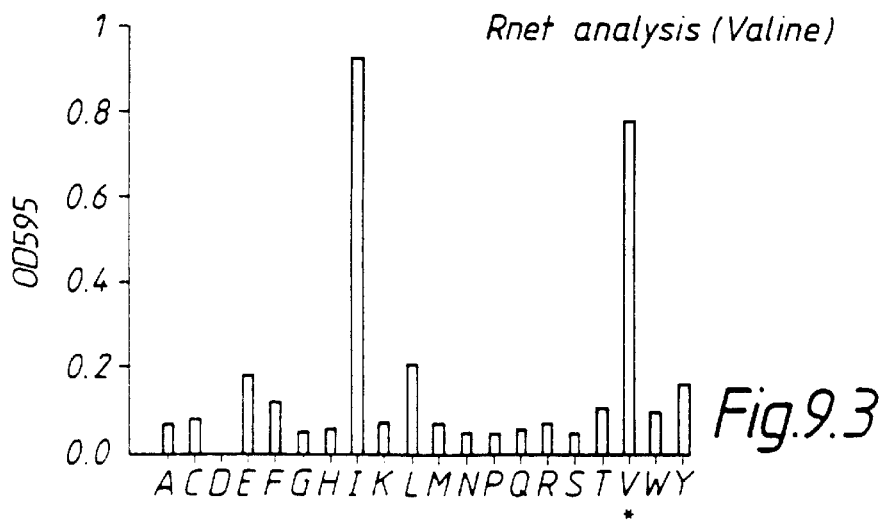
Fig. 9.3

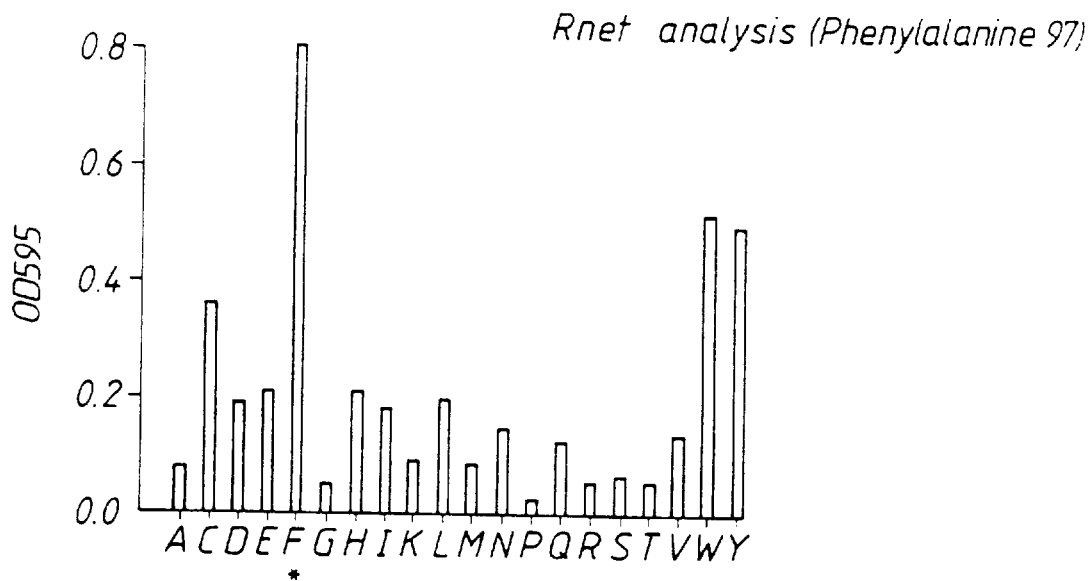
Fig.9.4
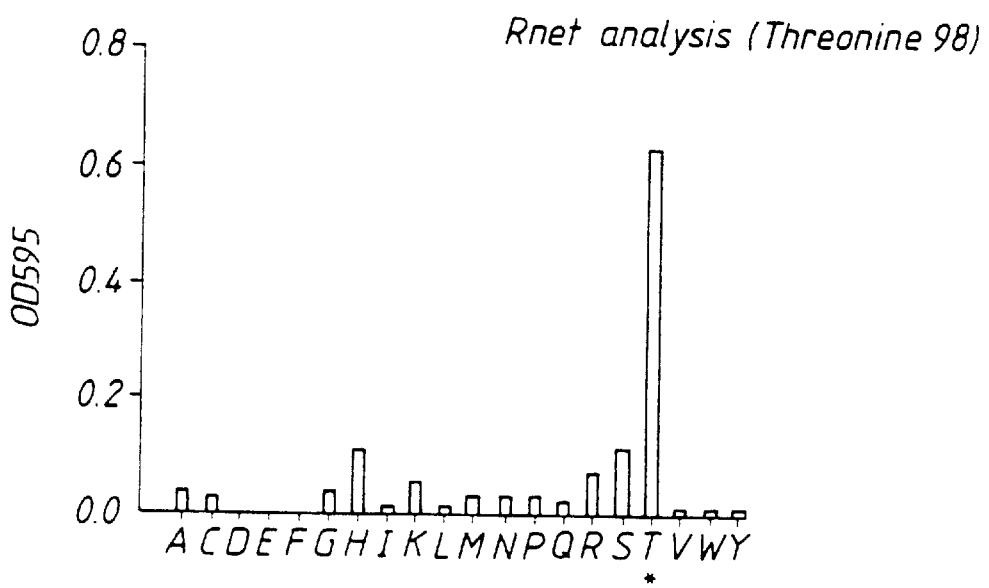
Fig.9.5

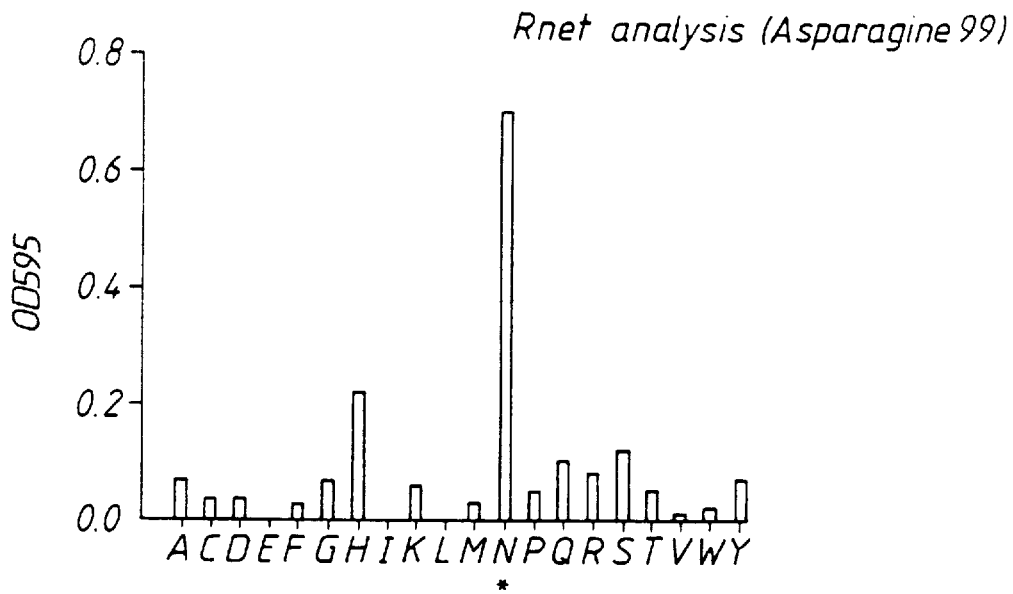
Fig. 9.6
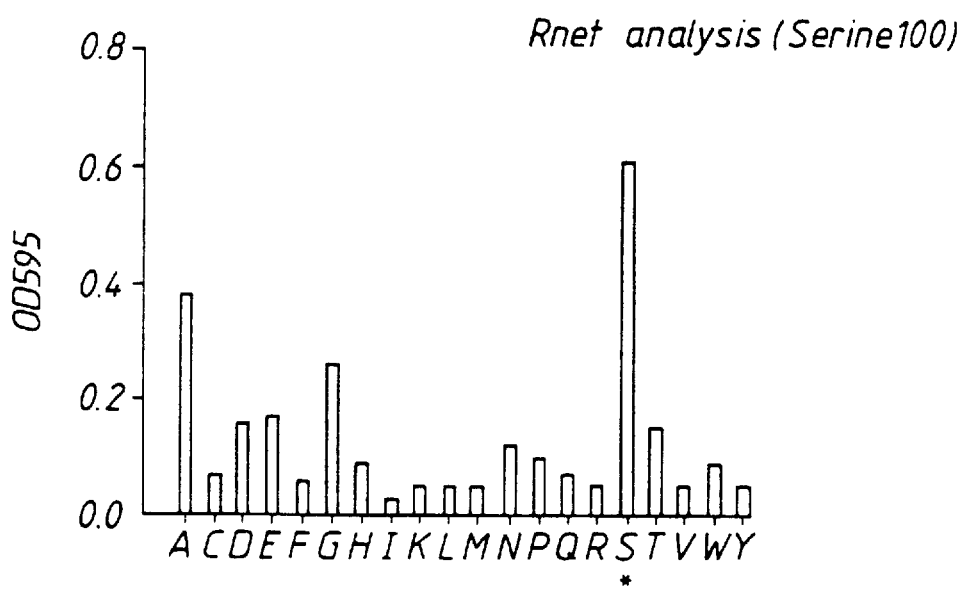
Fig. 9.7

GROWTH HORMONE POTENTIATING MOLECULES

The present invention relates to biologically active molecules, particularly peptides. More particularly, the invention relates to peptide fragments of growth hormone (including bovine growth hormone (bGH), porcine growth hormone (pGH), chicken growth hormone (cGH), ovine growth hormone (oGH) and their mutant derivatives), which are rendered antigenic and which can enhance or promote growth hormone activity. Human growth hormone (hGH), rat growth hormone (rGH), mouse growth hormone (mGH), horse growth hormone (eGH) and salmon growth hormone (sGH) are other growth hormones of interest.

Polypeptide hormones are important for both medical and veterinary application. One such hormone, growth hormone, is found in vertebrates and is important for promoting somatic growth. Growth hormones from different species share both structural and functional characteristics. Growth hormones consist of amino acid sequences generally of about 191 residues in length. It is known that growth hormone can stimulate somatic growth, promote wool growth in sheep, affect body composition, improve food efficiency and promote lactation in appropriate species. Different aspects of the structural and functional characteristics of growth hormones have been described (Nicoll et al, *Endocrine Rev.* 7(2) 169–203 (1986); Isaksson et al, *Ann. Rev. Physiol.* 47 483–499 (1985); Wallis, "Chemistry and Biochemistry of Amino Acids, Peptides and Proteins" (Ed. B. Weinstein), Vol. 5, pp 213–320 (Dekker, New York (1978)).

Antibodies to hormones have been shown to be capable of (i) enhancing hormone activity, (ii) have no effect on hormone activity or (iii) inhibit hormone activity (Thompson, *Proc. Soc. Expl. Biol. NY* 35 640–644 (1937); Rolands, *J. Endocrinol.* 1 177–183 (1939); Goodfriend et al, *J. Clin. Endocrinol. Metab.* 30 565–572 (1970); Schechter et al, *Proc. Natl. Acad. Sci. USA* 76(6) 2720–2724 (1979); Schechter et al, *Nature* 278 835–838 (1979); Cole et al, *Biol. Reprod.* 12 516–521 (1975); Aston et al, *J. Endocrinol.* 110 381–388 (1986); Aston et al, *Molec. Immunol.* 24 143–150 (1987); Ferguson, *Nature* 174 411 (1954)). More specifically, Aston et al 1986, 1987 loc. cit. have shown that certain antibodies to growth hormones can enhance the biological activity of the hormone in vivo. It was concluded in these studies that enhancement of hormone by antibodies is characteristic of particular specificities, a property also described previously (Cole et al 1975 loc. cit.; Goodfriend et al 1970 loc. cit.). However, in none of these studies is a regime available to indicate how to generate reproducibly an enhancing antiserum by using a small peptide. EP-A-0137234 discloses that the large 7 kiloDalton fragment of growth hormone can produce antibodies that enhance growth hormone activity; however, this fragment may not always be suited for this purpose due to its size and its limited ability to produce a consistent enhancing antiserum. Currently, manufacture of such a large polypeptide may be problematic by peptide synthetic routes.

Enhancement of hormonal activity by the administration of a peptide fragment of GH has been disclosed in WO-A-8404915. In this particular disclosure it was shown that a short peptide derived from the amino terminal portion of the GH molecule potentiated hypoglycaemic activity; however this peptide was not administered in an immunogenic fashion. Both GH and insulin induce hypoglycaemia when administered to animals. The insulin-potentiating activity of peptide fragments of GH have also been described elsewhere (Pullin et al, *Int. J. Peptide Protein Res.* 18 318–323 (1981); Ng. et al, *Diabetes* 29 782–787 (1980)).

More recent contributions to the art have included the identification of various sequence fragments of natural growth hormones which, when made appropriately antigenic (for example by coupling them to a suitable carrier) have the capability of enhancing or potentiating the activity of endogenous or exogenous growth hormone. For example: WO-A-8807547 identifies the 35 to 53 region of natural growth hormones; WO-A-8901166 identifies the 112–159 region in general and the smaller regions 120–140 and 134–154. more specifically; and EP-A-0303488 identifies the 1–18, 55–72, 97–110 and 122–138 regions generally but focuses attention on the 122–138, 119–131, 130–143, 123–137 and 133–146 regions. More recently still, Aston et al (*Molecular Immunology* 28 (1/2) 41–50 (1991)) confirmed the significant enhancement of hormonal activity by antibodies raised against the 120–140 and 134–154 regions, as well as other regions within the overall 112–159 region.

Significantly, though, Aston et al 1991 report a marked absence of growth hormone enhancing activity in antigenic peptides derived from the sequences immediately upstream (ie, towards the amino terminus) of the 112–159 sequence. Specifically, no enhancement at all was observed for the 80–100 sequence, and only a slight enhancement was seen for the 95–115 sequence which probably reflects the partial overlap with the 112–159 sequence.

It would still be desirable to identify further regions or sequences of growth hormones which give rise to antigenic peptides for enhancing growth hormone activity. This is the goal to which the present invention is addressed.

The invention is based on the surprising discovery that, in spite of the teaching of Aston et al 1991 discussed above, there is a region of growth hormone, not far upstream of the 112–159 region, which can form the basis of antigenic peptides which give rise to enhancement of growth hormone activity.

According to a first aspect of the invention, there is provided an antigenic molecule which causes antibodies to be raised against at least some of the 91 to 102 region of a natural growth hormone. This may be achieved by providing a molecule having antigenic equivalence to at least part of the 91 to 102 region.

According to a second aspect of the invention, there is provided a molecule (other than a natural growth hormone) at least part of which is antigenically equivalent to an oligopeptide selected from residues 91 to 102 of a natural growth hormone.

The 91 to 102 regions of various natural growth hormones have the following amino acid sequences:

| (bovine)  | bGH | QFLSRVFTNSLV | (SEQ ID NO: 1) |
|-----------|-----|--------------|----------------|
| (human)   | hGH | QFLRSVFANSLV | (SEQ ID NO: 2) |
| (porcine) | pGH | QFLSRVFTNSLV | (SEQ ID NO: 1) |
| (ovine)   | oGH | QFLSRVFTNSLV | (SEQ ID NO: 1) |
| (equine)  | eGH | QLLSRVFTNSLV | (SEQ ID NO: 3) |
| (mouse)   | mGH | QFLRSVFANSLV | (SEQ ID NO: 2) |
| (chicken) | cGH | QYLSKVFTNNLV | (SEQ ID NO: 4) |
| (rat)     | rGH | QFLSRIFTNSLV | (SEQ ID NO: 5) |
| (salmon)  | sGH | QTL-----NSLL | (SEQ ID NO: 6) |

Bovine, ovine, porcine and chicken growth hormones are preferred. Ovine growth hormone is very similar to bGH.

In the above, and throughout this specification, the amino acid residues are designated by the usual IUPAC single letter nomenclature. The single letter designations may be correlated with the classical three letter designations of amino acid residues as follows:

| | | | | | | | |
|---|---|---|---|---|---|---|---|
| A = | Ala | G = | Gly | M = | Met | S = | Ser |
| C = | Cys | H = | His | N = | Asn | T = | Thr |
| D = | Asp | I = | Ile | P = | Pro | V = | Val |
| E = | Glu | K = | Lys | Q = | Gln | W = | Trp |
| F = | Phe | L = | Leu | R = | Arg | Y = | Tyr |

The oligopeptide will be of at least the minimum size necessary to confer epitope specificity: usually it will be of at least six or seven residues, but may be of any suitable length up to, for example, 20 amino acid residues. The best oligopeptides may be expected to correspond to topographical surface features of a natural growth hormone molecule, that is to say those features having some three-dimensional feature protruding from or extending into the ambient surface level of the hormone. Preferred oligopeptides correspond to regions 94–98.

Probably the most simple way of ensuring that at least part of the molecule is antigenically equivalent to the oligopeptide is for that part of the molecule to comprise a sequence of amino acid residues which is identical to or conformationally similar to the oligopeptide. However, any other way of producing antigenic equivalence may be used: an example is to use an anti-idiotype antibody or other (even non-proteinaceous) analogue.

The invention therefore encompasses antigenic molecules including short peptides (preferably of less than 10 amino acid residues, but generally of at least 4 or 5 amino acid residues, for example 6 to 8 residues) sharing structural homology with growth hormone and which when administered to an animal can enhance hormone activity. Potentiation of hormone activity (in particular growth hormone activity), may occur through direct or indirect effects on the hormone in question. Non-antigenic peptides are useful as chemical intermediates in the preparation of antigenic peptides and are also within the scope of the invention.

The invention therefore encompasses a peptide other than a natural growth hormone comprising the amino acid sequence (SEQ ID NO: 1):

QFLSRVFTNSLV or an active fragment thereof and/or conservative mutant thereof. This sequence is taken from oGH, residues 91 to 102, and is identical to pGH and bGH. Peptides comprising amino acid sequences corresponding to this region from other growth hormones are also within the scope of the invention.

Prior to administration the peptide will generally be rendered antigenic and capable of stimulating the production of antibodies which, when in an appropriate formulation, potentiate the effect of growth hormone.

As stated above, an active subfragment of the specified sequence may be used. Active subfragments may consist of or include pentapeptides, including (in the case of oGH) one or more of:

| | |
|---|---|
| QFLSR | (SEQ ID NO: 7) |
| FLSRV | (SEQ ID NO: 6) |
| LSRVF | (SEQ ID NO: 9) |
| SRVFT | (SEQ ID NO: 10) |
| RVFTN | (SEQ ID NO: 11) |
| VFTNS | (SEQ ID NO: 12) |
| FTNSL | (SEQ ID NO: 13) |
| TNSLV. | (SEQ ID NO: 14) |

Active subfragments may also consist of or include hexapeptides, including one or more of:

| | |
|---|---|
| QFLSRV | (SEQ ID NO: 15) |
| FLSRVF | (SEQ ID NO: 16) |
| LSRVFT | (SEQ ID NO: 17) |
| SRVFTN | (SEQ ID NO: 18) |
| RVFTNS | (SEQ ID NO: 19) |
| VFTNSL | (SEQ ID NO: 20) |
| FTNSLV. | (SEQ ID NO: 21) |

Active subfragments may alternatively consist of or include heptapeptides, including one or more of:

| | |
|---|---|
| QFLSRVF | (SEQ ID NO: 22) |
| FLSRVFT | (SEQ ID NO: 23) |
| LSRVFTN | (SEQ ID NO: 24) |
| SRVFTNS | (SEQ ID NO: 25) |
| RVFTNSL | (SEQ ID NO: 26) |
| VFTNSLV. | (SEQ ID NO: 27) |

Further, active subfragments may consist of or include octapeptides, including:

| | |
|---|---|
| QFLSRVFT | (SEQ ID NO: 28) |
| FLSRVFTN | (SEQ ID NO: 29) |
| LSRVFTNS | (SEQ ID NO: 30) |
| SRVFTNSL | (SEQ ID NO: 31) |
| RVFTNSLV. | (SEQ ID NO: 32) |

Preferred fragments include those containing some, for example at least four residues of, or all of the pentapeptide motif SRVFT (SEQ ID NO:10). Most preferred fragments contain from residues 94 to 100, which appears to be the minimum functional unit for optimal results. In ovine growth hormone, this motif comprises SRVFTNS (SEQ ID NO:25).

Each of the above sequences can be varied to take into account variations in the sequence of corresponding regions of growth hormones from other species, particularly those previously referred to. Sequences corresponding to the preferred oGH 94–100 sequence (SRVFTNS) (SEQ ID NO:25) are as follows:

| | | | | |
|---|---|---|---|---|
| (bovine) | bGH | 94–100 | SRVFTNS | (SEQ ID NO: 25) |
| (human) | hGH | 94–100 | RSVFANS | (SEQ ID NO: 33) |
| (porcine) | pGH | 94–100 | SRVFTNS | (SEQ ID NO: 25) |
| (equine) | eGH | 94–100 | SRVFTNS | (SEQ ID NO: 25) |
| (mouse) | mGH | 94–100 | RSVFANS | (SEQ ID NO: 33) |
| (chicken) | cGH | 94–100 | SKVFTNN | (SEQ ID NO: 34) |
| (rat) | rGH | 94–100 | SRIFTNS | (SEQ ID NO: 35) |

It should be noted that combinations of more than one of the above sequences may be used.

Although the use of natural sequences in an antigenic molecule can certainly lead to generation of appropriate antibodies, it is also the case that a non-natural sequence may give rise to an antibody which binds to a given natural sequence. It has been found, as part of the studies involved in the present invention, that an antibody which binds the preferred sequence SRVFTNS can bind certain modifications of that sequence almost as strongly and, in some cases, even more strongly than the natural sequence. It is therefore well within the scope of the invention to use such modified sequences in epitopes of antigenic molecules.

Generally, the natural 94–100 sequence and its acceptable variations may be set out as follows (SEQ ID NO:36):

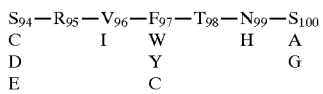

| $S_{94}$— | $R_{95}$— | $V_{96}$— | $F_{97}$— | $T_{98}$— | $N_{99}$— | $S_{100}$ |
|---|---|---|---|---|---|---|
| C | | I | W | | H | A |
| D | | | Y | | | G |
| E | | | C | | | |

In the above general formula, the natural sequence is shown as the top line, substitute amino acids are shown vertically aligned with the corresponding natural amino acid.

Replacement of $S_{94}$ with C, D or E appears to give better binding than the wild type sequence in the model system studied. Such replacements are therefore preferred over the wild type. D and E are preferable to C. Similarly, $V_{96}$ is preferably replaced by I as better binding results. Although, $F_{97}$ may be replaced by W, Y or (less preferably) C, it is preferred to keep the natural residue at this position. $N_{99}$ is the residue of choice at position 99, but H may be substituted. $S_{100}$ may be replaced by G or, preferably, A, but the natural residue is preferred.

Bearing the above comments in mind, a subset of the natural 94–100 sequence and its preferred variations may be set out as follows (SEQ ID NO:37).

| $S_{94}$— | $R_{95}$— | $V_{96}$— | $F_{97}$— | $T_{98}$— | $N_{99}$— | $S_{100}$ |
|---|---|---|---|---|---|---|
| C | | I | | | | |
| D | | | | | | |
| E | | | | | | | of course, more than one substitution may be made.

According to a further aspect of the invention, a method of promoting the activity of growth hormone (or a substance having growth hormone activity) comprises administering to a vertebrate an effective amount of an antigenic peptide or other molecule as described above. The invention thus encompasses the use of a peptide or other molecule as described above in the preparation of an agent for use in the promotion of the activity of growth hormone or a substance having growth hormone activity.

Peptides and other molecules in accordance with the invention may be rendered antigenic, or presented, in a variety of ways. For preference, an antigenic region (such as a peptide fragment or sub-fragment) in a molecule in accordance with the invention will contain the amino acid sequence of choice linked to a carrier peptide or protein. It is generally preferred to have a plurality, for example 5 to 10, copies of a peptide sequence (for example one or more of the above sequences) linked to the carrier. The carrier can for convenience be a generally large protein, which is inert in material respects, and which is derived from a different species or genus from that associated with the natural growth hormone. Examples of carriers include albumins such as human serum albumin, bovine serum albumin and ovalbumin (although not so many peptides will probably be able to be carried in this last case). Alternatively, keyhole limpet haemocyanin can be used. The carrier will generally preferably come from a different species from that on which the fragment is based.

It is not essential that peptide sequences as described above be linked to albumins: they may be linked to other macromolecules, such as β-galactosidase, especially of bacterial origin.

The invention encompasses molecules being peptides or having peptide regions which share substantial (eg greater than 30%, 50% or even 70%) sequence homology with the above peptides. Similarly, conservative amino acid substitutions may not decrease the immunogenicity or antigenicity of peptides. Thus antigenically similar homologues will elicit antibody which binds to GHs in the same region as the above peptides define. It is well known that the use of homologues can be a means of circumventing 'self' tolerance. Thus the use of the corresponding sequences from other species may be advantageous in this invention. Examples of homologous sequences to the preferred bovine, porcine and ovine growth hormones are those derived from the corresponding sequence regions of equine GH, mouse GH, chicken GH, trout or salmon GH or rat GH.

It is alternatively possible for molecules in accordance with the invention which are or which comprise peptides to be or to include polymers of sequences as described above. Appropriate sequences can be polymerised either by cross-linking of two cysteine residues to form disulphide bonds or by using external chemical coupling agents (such as carbodiimide, glutaraldehyde or other dialdehydes or di- (or poly-) functional carboxylic acids). As a further alternative, recombinant DNA techniques could be used to produce a peptide polymer.

It should be noted that the chemical coupling (which could for example take place through the agency of lysine residues) and disulphide bond formation are not limited to when the coupling residues are at the end of the sequence: internal residues could also be appropriate. Coupling residues, for example cysteine residues, may be added as desired.

It may be found that it is not necessary to couple any of the sequences described above with external peptides.

They may be antigenic on their own. In such a case, it may be advisable to select particular adjuvants such as DEAE DEXTRAN adjuvant and MERCK 7426 adjuvant.

According to a further aspect of the present invention, there is provided a pharmaceutical or veterinary composition comprising an antigenic molecule as described above in conjunction with a pharmaceutically or veterinarily acceptable carrier. The composition may contain an adjuvant, for example, DEAE DEXTRAN adjuvant and MERCK 7426 adjuvant, a muramyl peptide compound such as muramyl dipeptide, saponin and aluminium hydrogel. Alternatively or in addition Freund's complete adjuvant could be used. As noted above, certain adjuvants are more likely to be preferred in particular circumstances.

Compositions in accordance with the invention will normally be sterile, as they will be intended for implantation or injection. Intravenous injection is not preferred: subcutaneous injection is the route of choice, although possibly intramuscular and/or intraperitoneal injection could be used.

The preferred location of the subcutaneous injection would be at the back of the neck in the case of an animal, as that is a place where commercially useful meat is less likely to be damaged by tissue breakage or bruising.

The carrier will generally be an isotonic buffer plus is saline, such as PBS or physiological saline.

Dosages will be generally as prescribed in accordance with the directions of the physician or veterinary surgeon, but 5 to 500 μg per dose, particularly 50 to 100 μg of peptide or other molecule may be found to be suitable for bovine or porcine applications.

A substance having or promoting growth hormone activity can be administered shortly after (or may be in some circumstances prior to or at the same time as) peptides or other molecules in accordance with the present invention. The activity of the growth hormone is then enhanced. This can lead to enhanced growth where growth is relevant; improved body compositions (for example, in pigs there may be less fat and more muscle on the back); better wool growth in sheep; improved growth efficiency (that is to say, better growth for a given unit amount fed); and enhancement of lactation in cows and sheep. This latter application is not only important for providing milk or human consumption, but it may also enable sheep to rear their young more effectively.

Examples of substances promoting growth hormone activity other than growth hormones themselves and other than molecules in accordance with this invention include antibodies to growth hormone inhibitors and antibodies to other growth hormone antagonists, such as antibodies against somatostatin or leutinising hormone releasing hormone (LHRH). The production of an antibody to somatostatin, for example, would increase circulating GH levels and may thus potentiate the effect of molecules in accordance with the present invention. Another substance which may be regarded as promoting growth hormone activity is growth hormone releasing hormone (GRF), which may also be administered.

In another aspect, the invention provides antibodies raised against, or otherwise capable of specifically binding to, molecules of the first aspect. Such antibodies may be parenterally administered to animals, generally in an appropriate formulation to produce a growth hormone potentiating effect. Preferred formulation and administration details may be as described above, with changes as appropriate.

BRIEF DESCRIPTION OF THE DRAWINGS

The invention will now be illustrated by the following examples. The examples refer to the accompanying drawings, in which:

FIG. 2(a) relates to Example 1 and shows oGH residues 91 to 102;

FIG. 2(b) relates to Example 1 and shows overlapping octapeptides corresponding to the region shown in FIG. 2(a);

FIG. 3 relates to Example 2 and shows the dose response effect of MAb OA15 in enhancing the oGH-mediated increase in $^{35}SO_4^{2-}$ uptake into costal cartilage of Snell dwarf mice;

FIGS. 6.1 to 6.5 relate to Example S and show that each of five sheep produced an antiserum capable of recognising $^{125}I$-bGH in a liquid phase radio-immunoassay;

FIG. 8 relates to Example 6 and shows the results of a window size analysis of the OA15 epitope of oGH; and FIGS. 9.1 to 9.7 relate to Example 6 and show the results of a replacement net analysis of the OA15 epitope of oGH.

EXAMPLE 1

Figure 1:
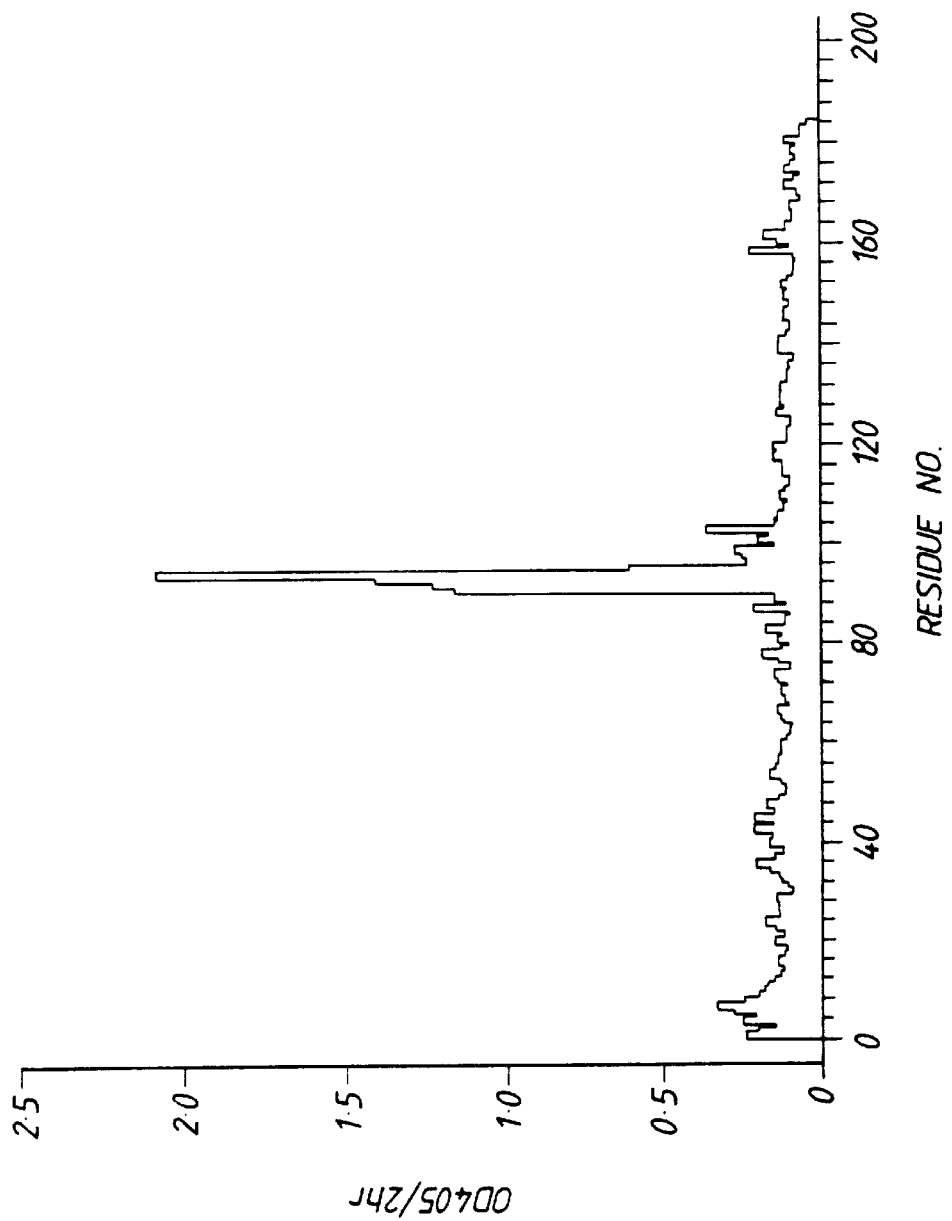
FIG. 1 relates to Example 1 and is an epitope scan of monoclonal antibody (MAb) OA15, which binds to a continuous antigenic determinant on oGH located between residues 91 and 102.

Epitope Scan of oGH Using MAb (OA15)

Ovine GH (oGH) was prepared as described previously by Aston et al (*Mol. Immunol.* 24 143–150 (1987)); porcine GH (pGH) was obtained from the USDA (batch 20705) pituitary hormone programme. Generation and characterisation of MAbs to oGH, including that designated OA15, and in vivo bio-assay of oGH and oGH-MAb complexes have also been described previously by Aston et al (1987) loc. cit. Amounts of MAb OA15 are expressed in $ABT_{50}$ values: this is the amount of MAb required to bind 50% of $^{125}I$-oGH by solution phase titration assay.

An adaptation of the multiple pin peptide synthesis method of Geysen et al (*Proc. Natl. Acad. Sci. USA* 81 3998–4002 (1984)) was used for epitope analysis, as follows. Briefly, octamers representing the entire sequence of rbGH were assembled with a one residue overlap onto activated polyethylene pins (ie 1–8, 2–9, 3–10, . . . 184–191). Peptides were synthesised on duplicate pins and therefore the 184 sets of octapeptides were accommodated on 4 blocks of 96 pins. The peptides were custom synthesized by Cambridge Research Biochemicals (Northwich, Cheshire, England). Mapping of the epitope recognised by MAb OA15 was performed as described below.

Pins were blocked by incubation for 1 hour at ambient temperature in a solution containing 2% (w/v) BSA, 0.1% (v/v) TWEEN 20 detergent in 10 mM phosphate buffered saline (PBS) pH 7.4. Following incubation, excess blocking solution was shaken from the pins and they were placed in a solution of first antibody (ie mouse MAb OA15 hybridoma S supernatant 0.6 mg/ml protein diluted 1:2000 in blocking buffer containing 0.1% (w/v) Na azide. 175 µl/well of first antibody was added and incubation was continued overnight at 4° C. Blocks of pins were then washed in a bath of 10 mM PBS (4×10 min washes) and incubated with appropriate second antibody-horse radish peroxidase (HRP) conjugate 175 µl/well of a 1:1000 dilution in a buffer containing 1% (v/v) normal sheep serum, 0.1% (w/v) sodium caseinate, 0.1% (v/v) TWEEN 20 detergent, in PBS pH 7.4. Pin blocks were washed (4×10 min) in 0.01M PBS as before and bound antibody was detected by immersion of pins in 150 µl/well of substrate buffer (0.1M $Na_2HPO_4$:0.1M citric acid pH 4) containing 0.05% (w/v) 2,2'-azino-bis-(3-ethylbenzthiazoline-6-sulphonic acid (ABTS), and 0.01% hydrogen peroxide. Colour development was monitored over a period of 30 min-2 hr and absorbances were determined at 405 nm. All antibody incubation and washing steps were performed on a flat-bed shaking table at 100 rpm.

After each epitope scan, antibody was removed from the pins by sonication for 10 min at 65° C. in a buffer containing 1% (w/v) SDS, 0.1% (v/v) 2-mercaptoethanol in 10 mM PBS pH 7.4. Pin blocks were then washed in distilled water at an initial temperature of 65° C. for 30min. Finally blocks were immersed in methanol at 60° C. for 15 sec, left to air dry and stored in the presence of silica gel dessicant at 4° C. This procedure for regeneration of peptides is also exactly in accordance with the manufacturer's instructions. In the applicants' studies pin blocks have been used 25 times with no observable decrease in antibody binding or increase in background absorbance. For MAb OA15, three epitope scans were performed at 1:2000. to confirm the efficient removal of antibody from pins control experiments using second antibody or HRP substrate buffer alone were performed periodically. These experiments gave values equivalent to the background obtained with non-immune antisera.

Figure 2C:
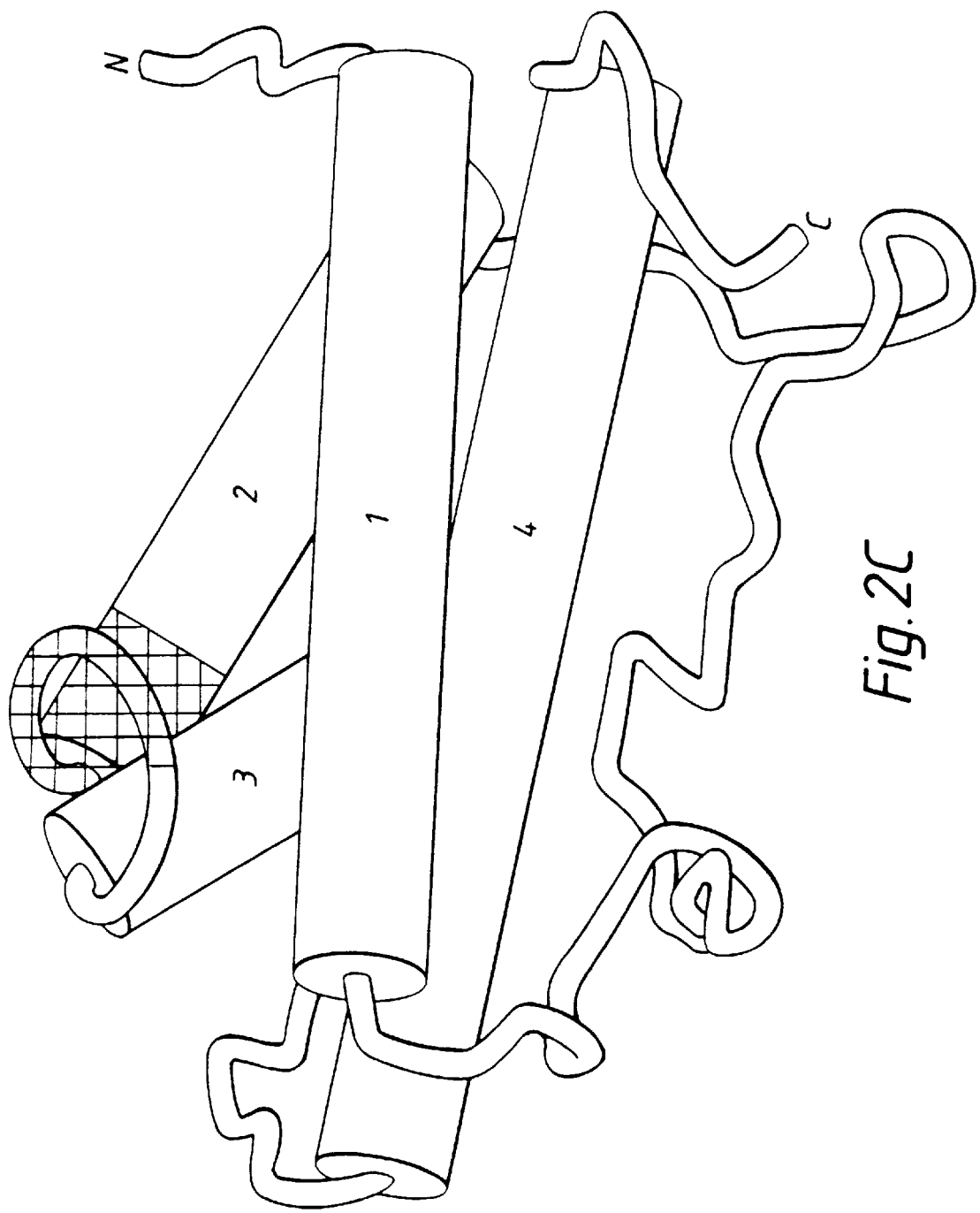
FIG. 2(c) relates to Example 1 and shows the location within the 3D structure of oGH of the epitope recognised by MAb OA15.

FIG. 1 shows the results of the epitope scan using MAb OA15. As is clearly evident, OA15 binds to a continuous antigenic determinant on the bGH molecule which is located between residues 91 and 102. In FIG. 2(a) the sequence of bGH fragment 91–102 is indicated. In FIG. 2(b), the sequences of the five overlapping pin-bound octapeptides derived from this region are shown, together with the relative reactivities of the peptides towards OA15. Also, shown boxed in FIG. 2(b) is a putative core recognition sequence which is shared amongst four of the five immunoreactive peptides. In FIG. 2(c) the location of this epitope is depicted diagrammatically within the three-dimensional structure of the molecule. This site comprises six residues from the C-terminal portion of helix 2 and the adjoining six residues from the region of random coil linking helices 2 and 3.

EXAMPLE 2

Enhancement of oGH Activity by OA15

FIG. 3 shows the dose-dependent enhancing effect of OA15 on oGH mediated $^{35}SO_4^{2-}$ incorporation into mouse costal cartilage (Holder et al, *J. Endocrinol* 85 35–47 (1980), Holder et al, *J. Endocrinol* 107 R9–R12 (1985)) when OA15 pre-bound to oGH is administered, compared to the results obtained with oGH (50 μg/day) alone. At the maximum dose of OA15 used (5000 $ABT_{50}$ units; approximately 100 μg pure MAb protein (Aston et al (1987) loc. cit.)) there was a 165% increase in $35so_4^{2-}$ uptake compared to the value obtained with oGH alone (15077±602 versus 5687±214 dpm $^{35}SO_4^{2-}$/mg costal cartilage). If the basal value for $^{35}SO_4^{2-}$ uptake (2140±137 dpm $^{35}SO_4^{2-}$/mg costal cartilage) is subtracted then this becomes a 3.5-fold increase with administration of OA15-oGH complex compared to administration of oGH alone.

EXAMPLE 3

Figure 4:
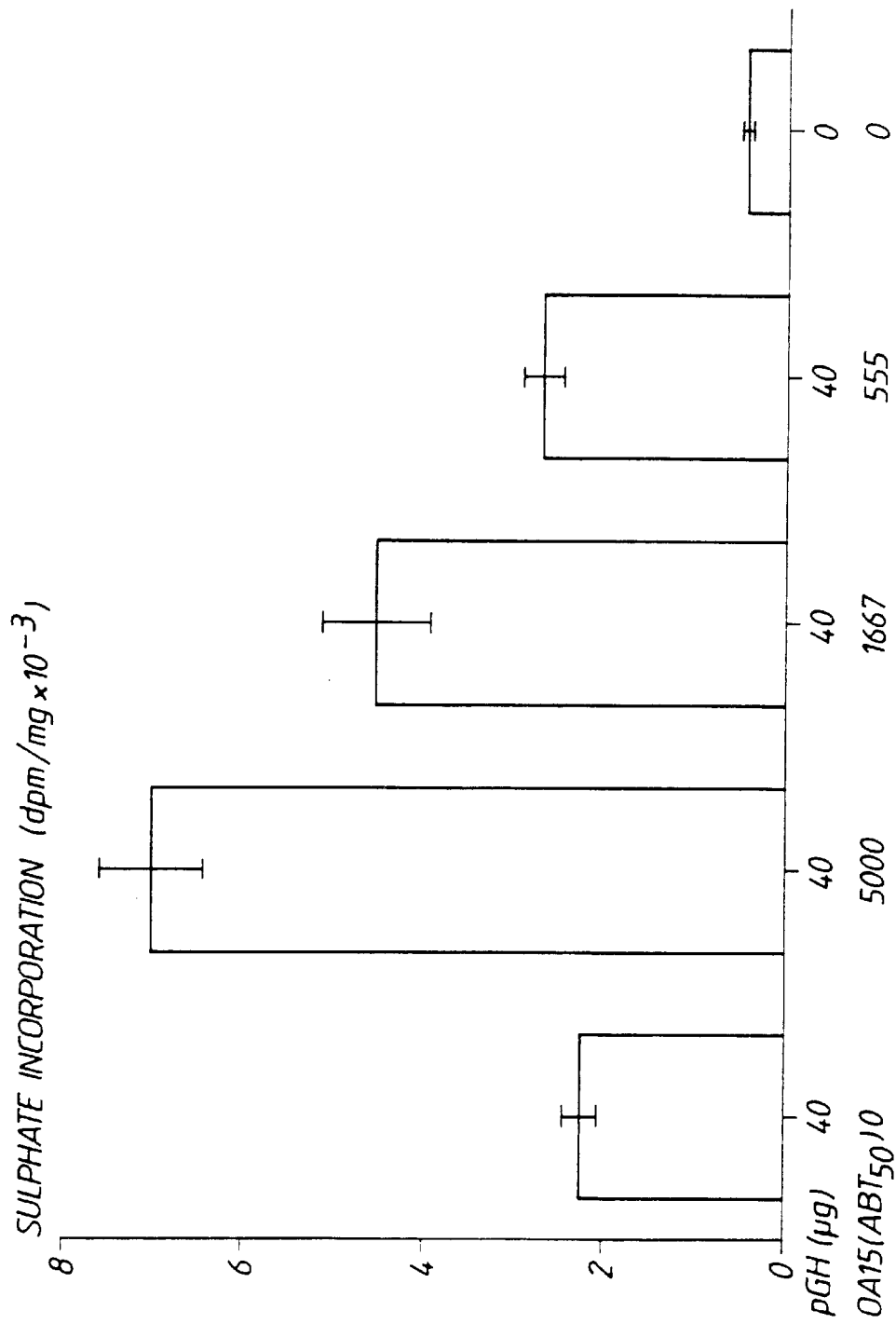
FIG. 4 relates to Example 3 and shows the dose response effect of MAb OA15 in enhancing the pGH-mediated increase in $^{35}SO_4^{2-}$ uptake into costal cartilage of Snell dwarf mice.

Enhancement of oGH Activity by OA15 pGH (40 μg/day) was substituted for oGH in Example 3 and administered to dwarf mice; similar results were obtained, as is shown in FIG. 4. At the maximum dose of OA15 (5000 $ABT_{50}$ units) there was a 212% increase in $^{35}SO_4^{2-}$ uptake compared to the value obtained with pGH alone (7022±580 vs. 2250±187 dpm $^{35}SO_4^{2-}$ per mg costal cartilage). If the basal value for $^{35}SO_4^{2-}$ uptake (460±60 dpm $^{35}SO_4^{2-}$ per mg costal cartilage) is subtracted then this becomes a 3.7-fold increase with administration of OA15-pGH complex compared to administration of pGH alone.

EXAMPLE 4

OA15 Binds oGH Remotely from the Receptor Binding Site

The contact area for OA15 on growth hormone is removed from those areas on growth hormone which are believed to be involved in receptor binding.

In a radio-receptor assay, pregnant rabbit liver membranes were prepared as described by Posner et al (*Endocrinol.* 95 521–531 (1974)): stock suspensions of membranes (approximately 20 mg/ml membrane protein) were diluted to 1 mg/ml in 20 mM $CaCl_2$—20 mM Tris Cl (pH 7.4): to 100 μl of this preparation (100 μg membrane protein) was added 100 μl $^{125}$I-oGH (20–30,000 cpm per tube) and 100 μl of various dilutions of OA15 MAb (■) or unlabeled oGH (●): tracer, unlabelled hormone and MAb dilutions were made in RRA buffer (20 mM Tris Cl (pH 7.4)—1% BSA—1% normal rabbit serum). Following overnight incubation at room temperature, 500 μl of 0.9% (w/v) NaCl was added, tubes centrifuged 1700 g for 30 min, supernatants decanted and bound radioactivity determined by γ-counting; oGH was iodinated to a specific activity of 50–100 μCi/μg by the iodogen coated tube method (Fraker and Speck, *Biochem. Biophys. Res. Comm.* 80 849–857 (1978)).

Figure 5:
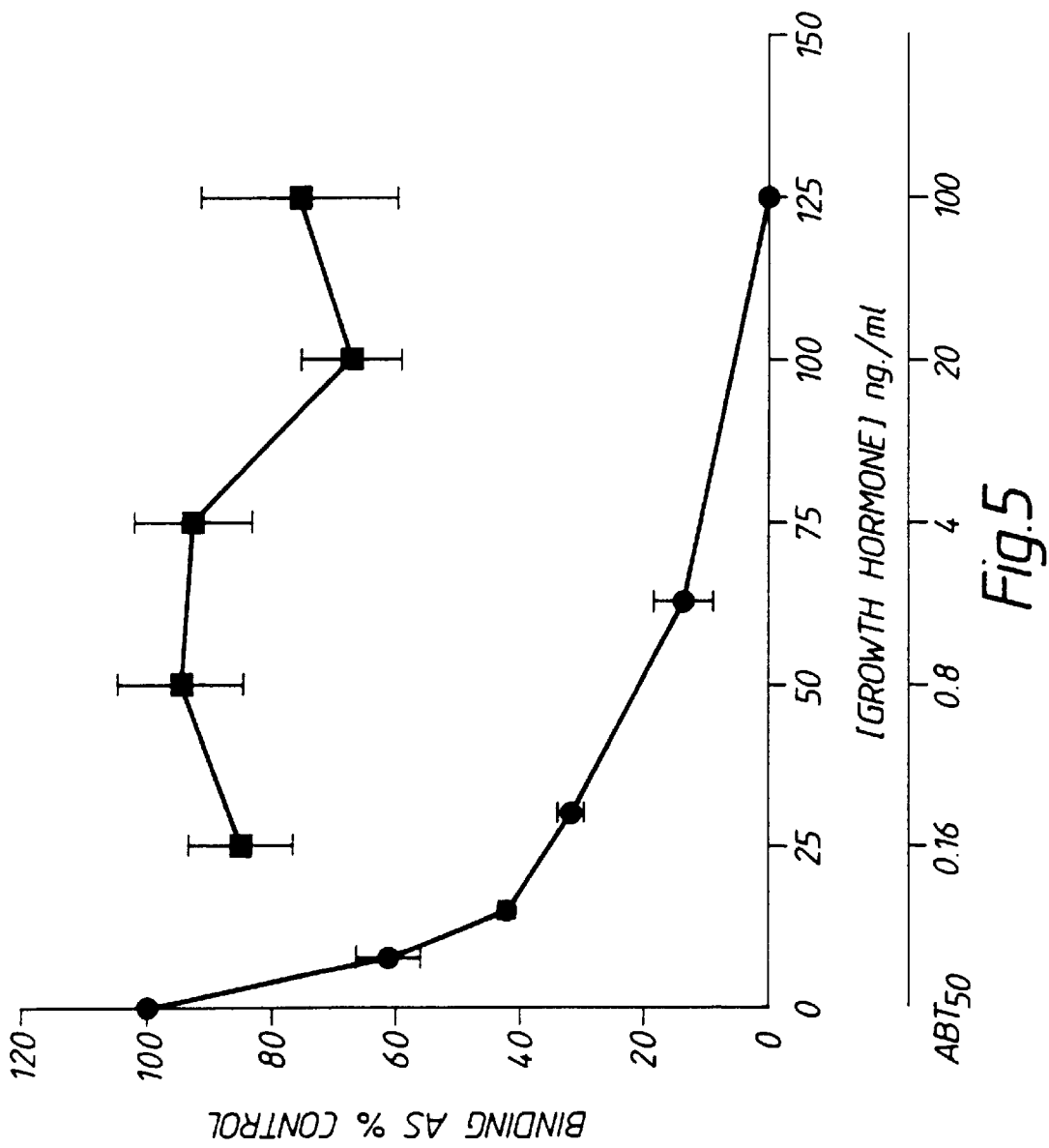
FIG. 5 relates to Example 4 and shows that MAb OA15 does not interfere with oGH binding to receptor.

The data presented in FIG. 5 show that OA15 failed to inhibit the binding of $^{125}$I-oGH to pregnant rabbit liver membrane microsomes.

EXAMPLE 5

Enhancement of oGH Activity by Polyclonal Antibodies

This example seeks to find whether the enhancing activity of OA15 shown in Examples 2 and 3 could be replicated by antisera prepared against the peptide which represents the epitope defined by MAb OA15. Sheep (n=5) were immunised with the 12-mer (Q F L S R V F T N S L V) (SEQ ID NO: 1) cross-linked to keyhole limpet haemocyanin (KLH) using glutaraldehyde, as follows.

The 12-mer peptide representing residues oGH 91–102-sequence Q F L S R V F T N S L V (SEQ ID NO: 1) was synthesised using solid phase F-moc chemistry on an Applied Biosystems 431A automated peptide synthesiser. Details of peptide synthesis, purification and characterisation are as described by Beattie and Flint (*Biochem. J.* 283 473–478 (1992)). Peptide was conjugated to keyhole limpet haemocyanin by addition of 50 μl 25% glutaraldehyde to 20 ml of 10 mM Na phosphate (pH 6.8) containing 0.5 mg/ml peptide and 0.5 mg/ml KLH. After stirring for 2–3 h at room temperature, the mixture was aliquoted, snap-frozen in liquid $N_2$ and stored at −20° C. prior to use. For immunisation, peptide-KLH conjugate was emulsified with an equal volume of Freunds' complete adjuvant and 1 ml (250 μg peptide equivalent) was injected into each hind leg of five sheep. Subsequent challenges were with 250 μg peptide in Freunds incomplete at 21 day intervals. Blood was taken prior to immunisation (A; Δ) and 10 days after each peptide immunisation (B; ○, C and D; □). Antibody production was monitored by the ability of serial dilutions of antisera to bind $^{125}$I-bGH in a liquid phase RIA. Each tube contained 50 μl antiserum, 50 μl $^{125}$I-bGH (prepared using iodogen ref. 28; 20,000 cpm/tube) and 100 μl of assay buffer. Tubes were incubated overnight at 4° C. and bound $^{125}$I-bGH was separated from free using PEG 6000. Each sheep antiserum is identified individually. There was no increase in titre after bleed C and these data have been omitted; serum from bleed C was used in subsequent experiments (see below). Results are means of triplicate determinations and background counts were not subtracted.

FIGS. 6.1 to 6.5 show that each of the five sheep produced an antiserum capable of recognising $^{125}$I-bGH in a liquid phase radioimmunoassay (RIA), and that titres increased with successive immunisations and bleeds (A, B, D)

Serum was prepared from blood taken from sheep H148 and HISS at bleed C. The immunoglobulin (Ig) fraction of the antisera was precipitated using $Na_2SO_4$ (Aston et al (*J. Endocrinol.* 110 381–88 (1986)); the precipitate was redissolved in a small quantity of PBS and dialysed extensively against PBS. The resulting antibody preparation was reconstructed to ½ the original serum volume and mixed with an equal volume of either bGH or pGH (USDA, Beltsville, Md., USA) such that the final solution contained 40 μg GH/0.1 ml. At this point antibody was present at physiological levels with regard to the concentration found in sheep serum. Dwarf mice (n=6/treatment group) were injected with 0.1 ml (sc) of GH/antibody complex or GH alone once/day for 2 days. On the third day mice received $^{35}SO_4^{2-}$ (0.5 μCi/g body wt ip), and were killed 20h later and $^{35}SO_4^{2-}$ uptake into costal cartilage measured. These methods have been described in more detail by Holder et al (*J. Endocrinol.* 85 35–47 (1980)). All results are expressed as means ±SEM. Differences between groups receiving GH plus antibody and the appropriate GH alone were assessed using students-t test (*p<0.05; ***p<0.001). Values in parentheses represent increases over the appropriate GH alone controls.

Figure 7:
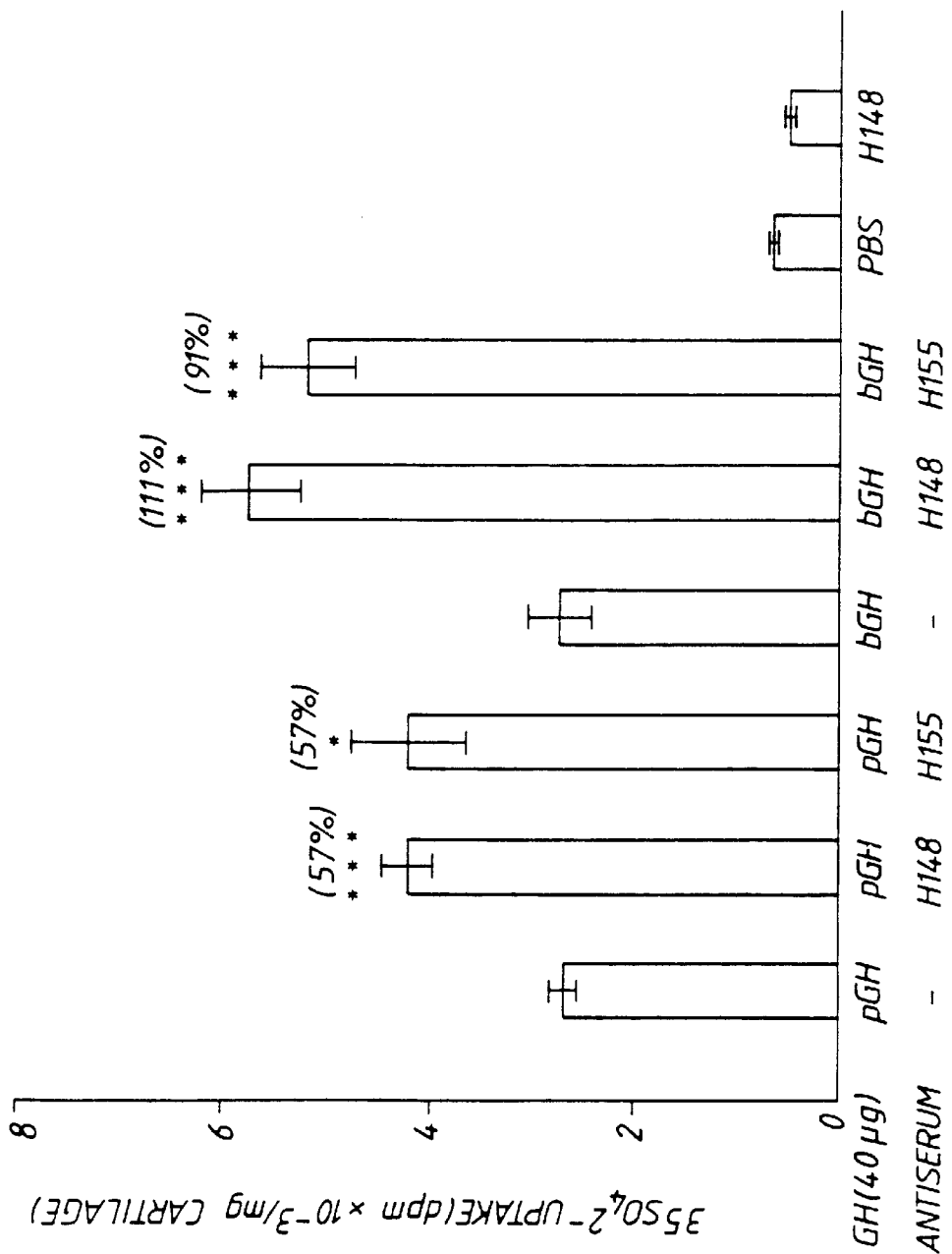
FIG. 7 relates to Example 5 and shows that anti-bGH antisera are capable of enhancing the biological actions of both bGH and pGH.

In FIG. 7 it is demonstrated that the antisera from sheep H148 and H155 (see FIGS. 6.2 and 6.3) are able to enhance the biological actions of both bGH and pGH, thus mimicking the properties of MAb OA15. The degree to which these antisera can enhance bGH and pGH (ie percent increases over the appropriate GH alone control) are given in parentheses (FIG. 7); it is apparent that the ability of these antisera to enhance bGH was greater than their ability to enhance pGH. This may be attributed to varying potencies of the GH preparations used. Preimmunisation sera from these animals failed to enhance GH action (data not shown). Enhancing activity of the other three antipeptide antisera was not tested but it is predicted that they would also enhance GH action.

EXAMPLE 6

Window Size and Replacement Net Analyses

In order to gain further insight into the structure of the OA15 epitope, "window size" and "replacement net" analyses on the OA15 epitope were conducted. For the window size analysis, completely overlapping sets of 5–8 mers from the dodecapeptide bGH 91–102 (Q F L S R V F T N S L V) (SEQ ID NO:1) were assembled covalently onto activated polyethylene pins and probed for OA15 binding in an identical manner to that described in Example 1. Sizing analysis of the epitope revealed that a 7-mer peptide was required for substantial binding to remain. Peptides 4–6 residues in length showed either no, or much reduced binding activity. Within the series of 7-mers, the heptapeptide S R V F T N S (SEQ ID NO:25) had binding activity comparable with the most strongly reactive octapeptides seen in this and in previous scans (such as FIG. 1). This heptapeptide may therefore be defined as the minimum functional epitope for OA15 (asterisked in FIG. 8). The contribution of each residue within the epitope to OA15 binding was examined by a replacement net analysis, where each amino acid of the epitope is systematically replaced with each of the other nineteen naturally occurring L-amino acids (FIG. 9). For each replacement, reactivity against the native heptapeptide is asterisked; reactivity against substituted peptides is indicated over the corresponding amino acid replacing the native residue; single-letter codes are used for amino acids, which have been arranged alphabetically. As indicated, for R95 and T98 little replacement is permitted and in the context of this epitope, these may be viewed as critical residues for OA15 binding. The remaining residues S94, V96, F97, N99 and S100 appear replaceable to a greater or lesser degree. For example V96 is replaceable only by isoleucine (but not to any great degree by leucine). This is a conservative substitution illustrating the importance of an aliphatic, hydrophobic side chain in this part of the epitope. The act that I but not L will replace V at this position indicates a further level of structural specificity in the requirement for a β-methyl substituted side chain. Similarly, F97 is best replaced by the two other aromatic side chains— tryptophan (W) and tyrosine (Y) although in this instance limited replaceability is seen by other amino acid side chains. The two serine residues in the epitope—S94 and S100 show different patterns of replaceability. S94 is replaceable by cysteine (C), aspartic acid (D) and glutamic acid (E). In fact heptapeptides containing D or E show substantially higher is binding to OA15 than the parent sequence. For S100, replaceability is allowed, to a lesser extent, by alanine (A) and glycine (G) and for a few other residues. Finally N99 is only replaceable to any extent by histidine.

We claim:

1. An antigenic molecule consisting of the amino acid sequence selected from:

Xaa Arg Xaa Xaa Thr Xaa Xaa     (SEQ ID No:36)

where

Xaa position 1 is Ser, Cys, Asp or Glu

Xaa position 3 is Val or Ile

Xaa position 4 is Phe, Trp, Tyr or Cys

Xaa at position 6 is Asn or His

Xaa position 7 is Set, Ala or Gly.

2. An antigenic molecule consisting of the amino acid sequence:

QFLSRVFINSLV     (SEQ ID No:1).

3. An antigenic molecule consisting of the amino acid sequence:

SRVFINS     (SEQ ID No:25).

4. An antigenic molecule consisting of an amino acid sequence selected from

Xaa Arg Xaa Phe Thr Asn Ser     (SEQ ID No:37), where

Xaa position 1 is Ser, Cys, Asp or Glu

Xaa position 3 is Val or Ile.

5. A conjugate molecule comprising an antigenic molecule selected from the group consisting of the amino acid sequence:

(b) QFLSRVFTNSLV     (SEQ ID No;1);

(c) SRVFT     (SEQ ID No:10);

(d) SRVFTNS     (SEQ ID No:25);

and, linked to an inert protein.

6. The conjugate of claim 5, wherein more than one antigenic molecule is linked to the inert protein.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..12
        ( D ) OTHER INFORMATION: /note= "91-102 REGION OF BOVINE
            PORCINE OR OVINE GROWTH HORMONE"

( x i ) SEQUENCE DESCRIPTION: SEQ ID NO:1:

Gln  Phe  Leu  Ser  Arg  Val  Phe  Thr  Asn  Ser  Leu  Val
    1                    5                              10

( 2 ) INFORMATION FOR SEQ ID NO:2:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..12
    ( D ) OTHER INFORMATION: /note= "91-102 REGION OF HUMAN OR MOUSE GROWTH HORMONE"

( x i ) SEQUENCE DESCRIPTION: SEQ ID NO:2:

```
Gln Phe Leu Arg Ser Val Phe Ala Asn Ser Leu Val
1               5                   10
```

( 2 ) INFORMATION FOR SEQ ID NO:3:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..12
    ( D ) OTHER INFORMATION: /note= "91-102 REGION OF EQUINE GROWTH HORMONE"

( x i ) SEQUENCE DESCRIPTION: SEQ ID NO:3:

```
Gln Leu Leu Ser Arg Val Phe Thr Asn Ser Leu Val
1               5                   10
```

( 2 ) INFORMATION FOR SEQ ID NO:4:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..12
    ( D ) OTHER INFORMATION: /note= "91-102 REGION OF CHICKEN GROWTH HORMONE"

( x i ) SEQUENCE DESCRIPTION: SEQ ID NO:4:

```
Gln Tyr Leu Ser Lys Val Phe Thr Asn Asn Leu Val
1               5                   10
```

( 2 ) INFORMATION FOR SEQ ID NO:5:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:

(A) NAME/KEY: Peptide
(B) LOCATION: 1..12
(D) OTHER INFORMATION: /note= "91-102 REGION OF RAT GROWTH HORMONE"

(xi) SEQUENCE DESCRIPTION: SEQ ID NO:5:

Gln Phe Leu Ser Arg Ile Phe Thr Asn Ser Leu Val
1               5                   10

(2) INFORMATION FOR SEQ ID NO:6:

(i) SEQUENCE CHARACTERISTICS:
(A) LENGTH: 7 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Peptide
(B) LOCATION: 1..7
(D) OTHER INFORMATION: /note= "91-102 REGION OF SALMON GROWTH HORMONE"

(xi) SEQUENCE DESCRIPTION: SEQ ID NO:6:

Gln Thr Leu Asn Ser Leu Leu
1               5

(2) INFORMATION FOR SEQ ID NO:7:

(i) SEQUENCE CHARACTERISTICS:
(A) LENGTH: 5 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Peptide
(B) LOCATION: 1..5
(D) OTHER INFORMATION: /note= "91-95 REGION OF OVINE GROWTH HORMONE"

(xi) SEQUENCE DESCRIPTION: SEQ ID NO:7:

Gln Phe Leu Ser Arg
1               5

(2) INFORMATION FOR SEQ ID NO:8:

(i) SEQUENCE CHARACTERISTICS:
(A) LENGTH: 5 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Peptide
(B) LOCATION: 1..5
(D) OTHER INFORMATION: /note= "92-96 REGION OF OVINE GROWTH HORMONE"

(xi) SEQUENCE DESCRIPTION: SEQ ID NO:8:

Phe Leu Ser Arg Val
1               5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..5
        ( D ) OTHER INFORMATION: /note= "93-97 REGION OF OVINE GROWTH HORMONE"

( x i ) SEQUENCE DESCRIPTION: SEQ ID NO:9:

Leu  Ser  Arg  Val  Phe
1                        5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..5
        ( D ) OTHER INFORMATION: /note= "94-98 REGION OF OVINE GROWTH HORMONE"

( x i ) SEQUENCE DESCRIPTION: SEQ ID NO:10:

Ser  Arg  Val  Phe  Thr
1                        5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..5
        ( D ) OTHER INFORMATION: /note= "95-99 REGION OF OVINE GROWTH HORMONE"

( x i ) SEQUENCE DESCRIPTION: SEQ ID NO:11:

Arg  Val  Phe  Thr  Asn
1                        5

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..5
    ( D ) OTHER INFORMATION: /note= "96-100 REGION OF OVINE GROWTH HORMONE"

( x i ) SEQUENCE DESCRIPTION: SEQ ID NO:12:

Val Phe Thr Asn Ser
1                  5

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..5
        ( D ) OTHER INFORMATION: /note= "97-101 REGION OF OVINE GROWTH HORMONE"

( x i ) SEQUENCE DESCRIPTION: SEQ ID NO:13:

Phe Thr Asn Ser Leu
1                  5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..5
        ( D ) OTHER INFORMATION: /note= "98-102 REGION OF OVINE GROWTH HORMONE"

( x i ) SEQUENCE DESCRIPTION: SEQ ID NO:14:

Thr Asn Ser Leu Val
1                  5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..6
        ( D ) OTHER INFORMATION: /note= "91-96 REGION OF OVINE GROWTH HORMONE"

( x i ) SEQUENCE DESCRIPTION: SEQ ID NO:15:

Gln Phe Leu Ser Arg Val
1                  5

(2) INFORMATION FOR SEQ ID NO:16:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (v) FRAGMENT TYPE: internal (ix) FEATURE:
    (A) NAME/KEY: Peptide
    (B) LOCATION: 1..6
    (D) OTHER INFORMATION: /note= "92-97 REGION OF OVINE GROWTH HORMONE"

(xi) SEQUENCE DESCRIPTION: SEQ ID NO:16:

Phe Leu Ser Arg Val Phe
  1               5

(2) INFORMATION FOR SEQ ID NO:17:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (v) FRAGMENT TYPE: internal (ix) FEATURE:
    (A) NAME/KEY: Peptide
    (B) LOCATION: 1..6
    (D) OTHER INFORMATION: /note= "93-98 REGION OF OVINE GROWTH HORMONE"

(xi) SEQUENCE DESCRIPTION: SEQ ID NO:17:

Leu Ser Arg Val Phe Thr
  1               5

(2) INFORMATION FOR SEQ ID NO:18:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (v) FRAGMENT TYPE: internal (ix) FEATURE:
    (A) NAME/KEY: Peptide
    (B) LOCATION: 1..6
    (D) OTHER INFORMATION: /note= "94-99 REGION OF OVINE GROWTH HORMONE"

(xi) SEQUENCE DESCRIPTION: SEQ ID NO:18:

Ser Arg Val Phe Thr Asn
  1               5

(2) INFORMATION FOR SEQ ID NO:19:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (v) FRAGMENT TYPE: internal ( i x ) FEATURE:
    ( A ) NAME/KEY: Peptide
    ( B ) LOCATION: 1..6
    ( D ) OTHER INFORMATION: /note= "95-100 REGION OF OVINE GROWTH HORMONE"

( x i ) SEQUENCE DESCRIPTION: SEQ ID NO:19:

Arg Val Phe Thr Asn Ser
1               5

( 2 ) INFORMATION FOR SEQ ID NO:20:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..6
    ( D ) OTHER INFORMATION: /note= "96-101 REGION OF OVINE GROWTH HORMONE"

( x i ) SEQUENCE DESCRIPTION: SEQ ID NO:20:

Val Phe Thr Asn Ser Leu
1               5

( 2 ) INFORMATION FOR SEQ ID NO:21:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..6
    ( D ) OTHER INFORMATION: /note= "97-102 REGION OF OVINE GROWTH HORMONE"

( x i ) SEQUENCE DESCRIPTION: SEQ ID NO:21:

Phe Thr Asn Ser Leu Val
1               5

( 2 ) INFORMATION FOR SEQ ID NO:22:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..7
    ( D ) OTHER INFORMATION: /note= "91-97 REGION OF OVINE GROWTH HORMONE"

( x i ) SEQUENCE DESCRIPTION: SEQ ID NO:22:

Gln Phe Leu Ser Arg Val Phe
1               5

( 2 ) INFORMATION FOR SEQ ID NO:23:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..7
        ( D ) OTHER INFORMATION: /note= "92-98 REGION OF OVINE GROWTH HORMONE"

( x i ) SEQUENCE DESCRIPTION: SEQ ID NO:23:

Phe  Leu  Ser  Arg  Val  Phe  Thr
1                    5

( 2 ) INFORMATION FOR SEQ ID NO:24:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..7
        ( D ) OTHER INFORMATION: /note= "93-99 REGION OF OVINE GROWTH HORMONE"

( x i ) SEQUENCE DESCRIPTION: SEQ ID NO:24:

Leu  Ser  Arg  Val  Phe  Thr  Asn
1                    5

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..7
        ( D ) OTHER INFORMATION: /note= "94-100 REGION OF OVINE, BOVINE, EQUINE OR PORCINE GROWTH HORMONE"

( x i ) SEQUENCE DESCRIPTION: SEQ ID NO:25:

Ser  Arg  Val  Phe  Thr  Asn  Ser
1                    5

( 2 ) INFORMATION FOR SEQ ID NO:26:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide (v) FRAGMENT TYPE: internal (ix) FEATURE:
    (A) NAME/KEY: Peptide
    (B) LOCATION: 1..7
    (D) OTHER INFORMATION: /note= "95-101 REGION OF OVINE GROWTH HORMONE"

(xi) SEQUENCE DESCRIPTION: SEQ ID NO:26:

Arg Val Phe Thr Asn Ser Leu
1                     5

(2) INFORMATION FOR SEQ ID NO:27:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..7
        (D) OTHER INFORMATION: /note= "96-102 REGION OF OVINE GROWTH HORMONE"

(xi) SEQUENCE DESCRIPTION: SEQ ID NO:27:

Val Phe Thr Asn Ser Leu Val
1                     5

(2) INFORMATION FOR SEQ ID NO:28:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..8
        (D) OTHER INFORMATION: /note= "91-98 REGION OF OVINE GROWTH HORMONE"

(xi) SEQUENCE DESCRIPTION: SEQ ID NO:28:

Gln Phe Leu Ser Arg Val Phe Thr
1                     5

(2) INFORMATION FOR SEQ ID NO:29:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..8
        (D) OTHER INFORMATION: /note= "92-99 REGION OF OVINE GROWTH HORMONE"

(xi) SEQUENCE DESCRIPTION: SEQ ID NO:29:

Phe Leu Ser Arg Val Phe Thr Asn 1               5

(2) INFORMATION FOR SEQ ID NO:30:

(i) SEQUENCE CHARACTERISTICS:
        (A) LENGTH: 8 amino acids
        (B) TYPE: amino acid
        (D) TOPOLOGY: linear (i i) MOLECULE TYPE: peptide (v) FRAGMENT TYPE: internal (i x) FEATURE:
        (A) NAME/KEY: Peptide
        (B) LOCATION: 1..8
        (D) OTHER INFORMATION: /note= "93-100 REGION OF OVINE
            GROWTH HORMONE"

(x i) SEQUENCE DESCRIPTION: SEQ ID NO:30:

Leu  Ser  Arg  Val  Phe  Thr  Asn  Ser
1               5

(2) INFORMATION FOR SEQ ID NO:31:

(i) SEQUENCE CHARACTERISTICS:
        (A) LENGTH: 8 amino acids
        (B) TYPE: amino acid
        (D) TOPOLOGY: linear (i i) MOLECULE TYPE: peptide (v) FRAGMENT TYPE: internal (i x) FEATURE:
        (A) NAME/KEY: Peptide
        (B) LOCATION: 1..8
        (D) OTHER INFORMATION: /note= "94-101 REGION OF OVINE
            GROWTH HORMONE"

(x i) SEQUENCE DESCRIPTION: SEQ ID NO:31:

Ser  Arg  Val  Phe  Thr  Asn  Ser  Leu
1               5

(2) INFORMATION FOR SEQ ID NO:32:

(i) SEQUENCE CHARACTERISTICS:
        (A) LENGTH: 8 amino acids
        (B) TYPE: amino acid
        (D) TOPOLOGY: linear (i i) MOLECULE TYPE: peptide (v) FRAGMENT TYPE: internal (i x) FEATURE:
        (A) NAME/KEY: Peptide
        (B) LOCATION: 1..8
        (D) OTHER INFORMATION: /note= "95-102 REGION OF OVINE
            GROWTH HORMONE"

(x i) SEQUENCE DESCRIPTION: SEQ ID NO:32:

Arg  Val  Phe  Thr  Asn  Ser  Leu  Val
1               5

(2) INFORMATION FOR SEQ ID NO:33:

(i) SEQUENCE CHARACTERISTICS:
        (A) LENGTH: 7 amino acids
        (B) TYPE: amino acid
        (D) TOPOLOGY: linear (i i) MOLECULE TYPE: peptide ( v ) FRAGMENT TYPE: internal ( i x ) FEATURE:
    ( A ) NAME/KEY: Peptide
    ( B ) LOCATION: 1..7
    ( D ) OTHER INFORMATION: /note= "94-100 REGION OF HUMAN OR MOUSE GROWTH HORMONE"

( x i ) SEQUENCE DESCRIPTION: SEQ ID NO:33:

Arg Ser Val Phe Ala Asn Ser
1               5

( 2 ) INFORMATION FOR SEQ ID NO:34:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..7
    ( D ) OTHER INFORMATION: /note= "94-100 REGION OF CHICKEN GROWTH HORMONE"

( x i ) SEQUENCE DESCRIPTION: SEQ ID NO:34:

Ser Lys Val Phe Thr Asn Asn
1               5

( 2 ) INFORMATION FOR SEQ ID NO:35:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..7
    ( D ) OTHER INFORMATION: /note= "94-100 REGION OF RAT GROWTH HORMONE"

( x i ) SEQUENCE DESCRIPTION: SEQ ID NO:35:

Ser Arg Ile Phe Thr Asn Ser
1               5

( 2 ) INFORMATION FOR SEQ ID NO:36:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..7
    ( D ) OTHER INFORMATION: /note= "MODIFIED 94-100 REGION OF GROWTH HORMONE: Xaa position 1 is Ser, Cys, Asp, or Glu
    Xaa position 3 is Val or Ile
    Xaa position 4 is Phe, Trp, Tyr, Cys
    Xaa position 6 is Asn or His Xaa position 7 is Ser, Ala, or Gly"

(x i) SEQUENCE DESCRIPTION: SEQ ID NO:36:

Xaa Arg Xaa Xaa Thr Xaa Xaa
1               5

(2) INFORMATION FOR SEQ ID NO:37:

(i) SEQUENCE CHARACTERISTICS:
  (A) LENGTH: 7 amino acids
  (B) TYPE: amino acid
  (D) TOPOLOGY: linear (ii) MOLECULE TYPE: peptide (v) FRAGMENT TYPE: internal (ix) FEATURE:
  (A) NAME/KEY: Peptide
  (B) LOCATION: 1..7
  (D) OTHER INFORMATION: /note= "MODIFIED REGION 94-100 OF
       GROWTH HORMONE: Xaa position 1 is Ser, Cys, Asp, or Glu
       Xaa position 3 is Val or Ile"

(x i) SEQUENCE DESCRIPTION: SEQ ID NO:37:

Xaa Arg Xaa Phe Thr Asn Ser
1               5